United States Patent
Guckenberger

(10) Patent No.: US 11,370,002 B2
(45) Date of Patent: Jun. 28, 2022

(54) CLEANING SYSTEM

(71) Applicant: Emack Industries, LLC, Hicksville, NY (US)

(72) Inventor: Kevin M. Guckenberger, Hicksville, NY (US)

(73) Assignee: Emack Industries, LLC, Hicksville, NY (US)

( * ) Notice: Subject to any disclaimer, the term of this patent is extended or adjusted under 35 U.S.C. 154(b) by 0 days.

(21) Appl. No.: 16/907,747

(22) Filed: Jun. 22, 2020

(65) Prior Publication Data

US 2021/0346919 A1 Nov. 11, 2021

Related U.S. Application Data

(60) Provisional application No. 63/020,524, filed on May 5, 2020.

(51) Int. Cl.
| | |
|---|---|
| *B08B 9/032* | (2006.01) |
| *B08B 7/04* | (2006.01) |
| *A61B 90/70* | (2016.01) |
| *B08B 5/02* | (2006.01) |

(52) U.S. Cl.
CPC ............ *B08B 9/0328* (2013.01); *A61B 90/70* (2016.02); *B08B 5/02* (2013.01); *B08B 7/04* (2013.01); *B08B 2209/032* (2013.01)

(58) Field of Classification Search
None
See application file for complete search history.

(56) References Cited

U.S. PATENT DOCUMENTS

| | | | | |
|---|---|---|---|---|
| 5,526,841 A | * | 6/1996 | Detsch ................. | A61C 1/0007 134/102.2 |
| 5,746,596 A | | 5/1998 | Gallant et al. | |
| 5,785,523 A | * | 7/1998 | Overmyer ............ | A61C 1/0076 422/28 |
| 6,177,018 B1 | | 1/2001 | Ruppenthal | |
| 6,253,964 B1 | * | 7/2001 | Rainey ................. | A61C 1/0076 222/148 |
| 2014/0301871 A1 | | 10/2014 | Rogers, Jr. | |
| 2017/0173228 A1 | | 6/2017 | Ehlert | |

(Continued)

FOREIGN PATENT DOCUMENTS

| JP | 2010-051557 | * | 3/2010 |
|---|---|---|---|
| KR | 10200060019890 | | 3/2006 |

OTHER PUBLICATIONS

Machine Translation of JP2010-051557 by Kitano et al., published Mar. 11, 2010.*

(Continued)

*Primary Examiner* — Mikhail Kornakov
*Assistant Examiner* — Ryan L Coleman
(74) *Attorney, Agent, or Firm* — Collard & Roe, P.C.

(57) ABSTRACT

A cleaning system and process for cleaning a medical system comprising at least one air source at least one cleaning solution source at least one rinsing solution source and at least one switch for switching between the at least one air source, the at least one cleaning solution source, and said at least one rinsing solution source. The process is configured to selectively provide the cleaning solution from the cleaning solution source, selectively provide the rinsing solution source, and selectively providing the air pressure to purge the lines of a medical/dental system.

9 Claims, 4 Drawing Sheets

(56) References Cited

U.S. PATENT DOCUMENTS

| | | |
|---|---|---|
| 2019/0076567 A1 | 3/2019 | Yang |
| 2019/0134682 A1* | 5/2019 | Overmyer ............... A01J 7/022 |
| 2020/0271382 A1 | 8/2020 | Radford et al. |
| 2021/0204797 A1 | 7/2021 | Hernandez et al. |

OTHER PUBLICATIONS

Final Office Action dated Aug. 23, 2021 for U.S. Appl. No. 17/174,360.
Non-Final Rejection dated Apr. 5, 2021 for U.S. Appl. No. 17/174,360.

* cited by examiner

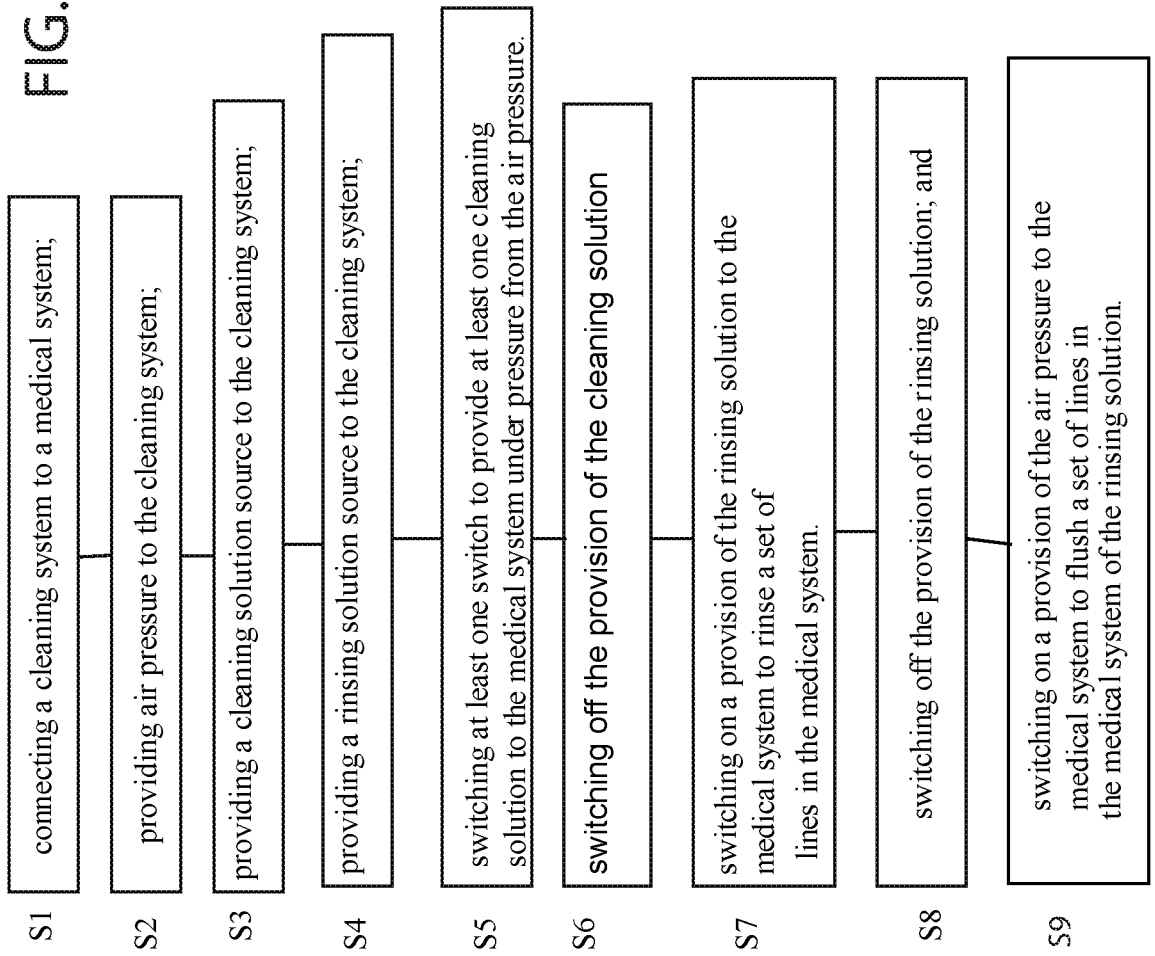

CLEANING SYSTEM

CROSS REFERENCE TO RELATED APPLICATIONS

This application is a non-provisional application that claims priority from U.S. Provisional Application Ser. No. 63/020,524 filed on May 5, 2020, the disclosure of which is hereby incorporated by reference.

BACKGROUND OF THE INVENTION

One embodiment of the invention relates to a cleaning system such as a dental cleaning system which is configured to be used for cleaning the lines of a dental office. This dental cleaning system can be used to essentially wash the inner lines of a dental service station.

Medical or dental systems which are first put into operation or which have laid dormant for an extended period of time can have a build up of biological material inside of the lines of the medical or dental system. The build up of biological material can be harmful for patients who are flushing their mouths with water that includes this biological material, it is beneficial to have the lines periodically flushed out via a cleaning system which is configured to efficiently clean these lines in a safe manner.

SUMMARY OF THE INVENTION

A cleaning system and process for cleaning a medical system comprising at least one air source at least one cleaning solution source at least one rinsing solution source and at least one switch for switching between the at least one air source, the at least one cleaning solution source, and said at least one rinsing solution source. The process is configured to selectively provide the cleaning solution from the cleaning solution source, selectively provide the rinsing solution source, and selectively providing the air pressure to a medical system.

A process for cleaning a medical system using a cleaning system comprising at least one air source, at least one cleaning solution source, at least one rinsing solution source, and at least one switch for switching between the at least one air source, the at least one cleaning solution source, and said at least one rinsing solution source.

The process comprises of connecting the cleaning system to the medical system so as to provide air pressure to the cleaning system. In another step the process includes providing a cleaning solution from cleaning solution source to the cleaning system. Another step involves providing a rinsing solution from said rinsing solution source to the cleaning system. One other step includes switching at least one switch to provide at least one cleaning solution, at least one rinsing solution or air pressure to the medical system.

BRIEF DESCRIPTION OF THE DRAWINGS

These and other benefits and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 4 is a process for cleaning a medical system.

DETAILED DESCRIPTION OF THE PREFERRED EMBODIMENTS

Figure 1:
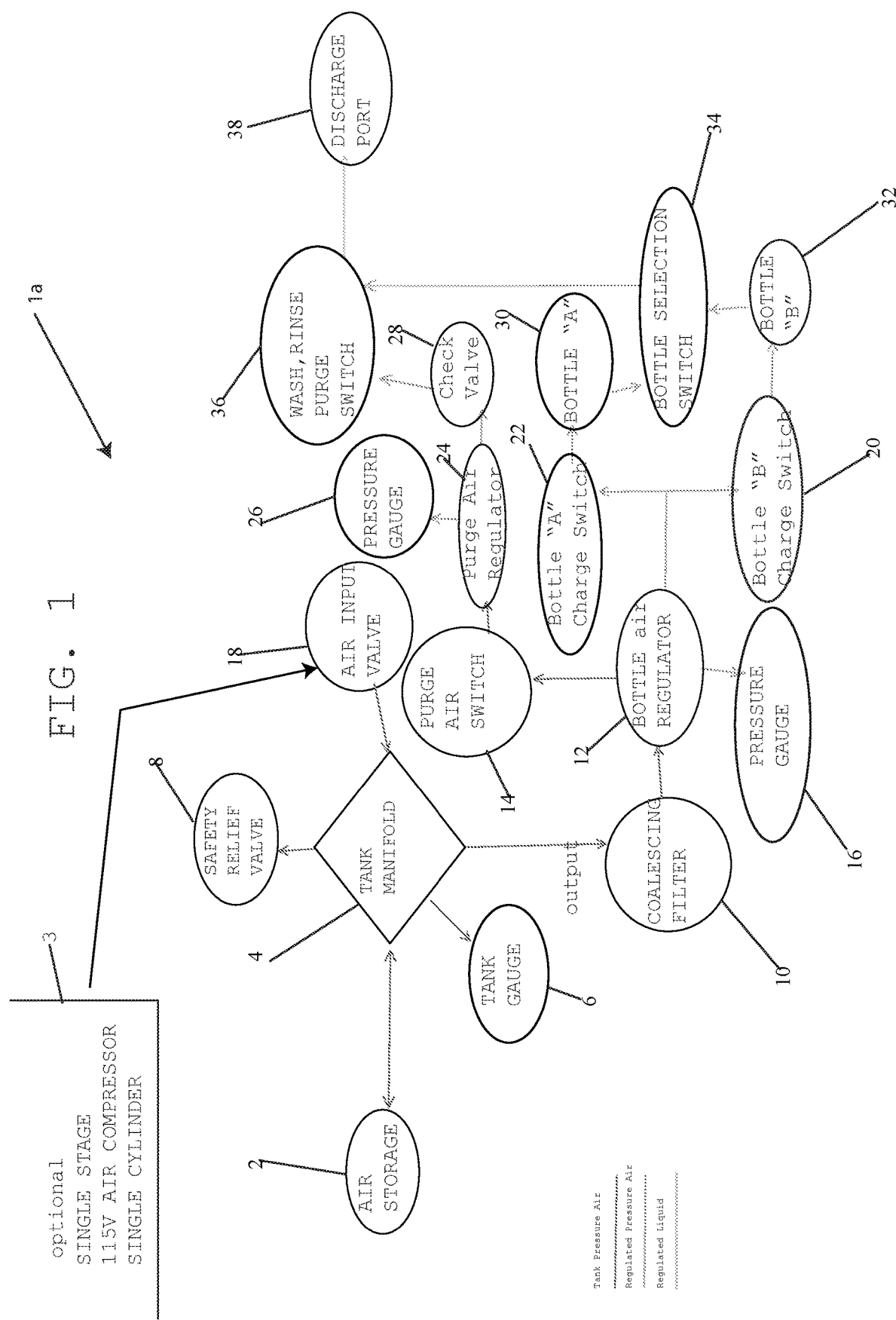
FIG. 1. shows a first block diagram of a first embodiment of the invention.

Referring now in detail to the drawings and, in particular, FIG. 1 shows a block diagram of a first embodiment 1a which includes an air pressure storage tank 2. While the storage tank can be of any suitable type, in at least one embodiment the tank is an aluminum 7 gallon tank. There is also an optional single stage air compressor 3 which is configured to provide air to the air storage 2. An output of air storage 2 is configured to connect to an input of tank manifold 4 which in at least one embodiment is at least a partially brass or similar type manifold which is configured to receive a plurality of different lines. Coupled to tank manifold 4 is a tank gauge 6 which reads the pressure in the tank manifold. There is also a safety relief valve 8 which is configured to relieve pressure in the system when air is of a pressure that is higher than a predetermined pressure. The air from single stage air compressor 3 and or air from the system located in the doctor's and/or dentist's office is configured to be input into the system via air input valve 18. Air flowing out from the manifold 4 is configured to flow through coalescing filter 10.

Air from coalescing filter 10 flows into bottle air regulator 12. Bottle air regulator 12 is configured to regulate the air pressure from the air storage 2 as well as provide regulated pressure to downstream bottles of either cleaning solution stored in a first bottle 30, or a rinsing solution in bottle 32. Bottle air regulator 12 has an output coupled to pressure gauge 16 and another output coupled to purge air switch 14 which is configured to selectively allow purging air pressure to flow through the tubes of the medical system. This purge air switch 14 is a toggle switch which allows the user to manually purge air through the system. As described above, the bottle air regulator 12 has its output which is fed into a charge switch 22 for the first bottle 30 containing the cleaning solution. In addition, air regulator 12 has its output which is fed into a charge switch 20 which has its output which feeds into a second bottle 32 which houses the rinse.

In at least one embodiment the cleaning solution comprises a bleach solution. In another embodiment, the cleaning solution comprises a bleach and further agent composite. In one embodiment the rinsing solution comprises water.

The output of the first bottle 30 containing the cleaning solution is fed into bottle selection switch 34. In addition, the second bottle 32 has its output which feeds into the bottle selection switch 34. The bottle selection switch 34 is configured to selectively allow fluid to flow into the wash, rinse and purge switch 36. The output of the wash, rinse and purge switch is fed into the discharge port 38. The discharge port is coupled to the medical or dental device which is then flushed with either the cleaning solution (such as a bleach solution), the rinsing solution (such as water) or air.

While pressure can be fed into the bottles 30 and 32 pressurizing the fluid in these bottles, the pressure such as air pressure can be fed as air from the purge air switch 14 into the purge air regulator 24. From the purge air regulator, the air flows into pressure gauge 26 to provide a reading of air pressure in the soon to be discharged air. The output of the purge air regulator 24 flows into the input of the check valve 28. The check valve 28 is configured as a backflow check valve which prevents fluid such as cleaning fluid or rinsing fluid to flow back into the air lines. Air flowing from the check valve 28 flows into the wash, rinse, and purge switch such that a user can then selectively elect to discharge pressurized air from the system to completely flush the lines of the medical and/or dental system with air.

While the lines in the cleaning system and in the medical and/or dental system can be of any type or shape, in at least one embodiment, the lines of this system are configured as ¼ inch poly tubing.

Figure 2:
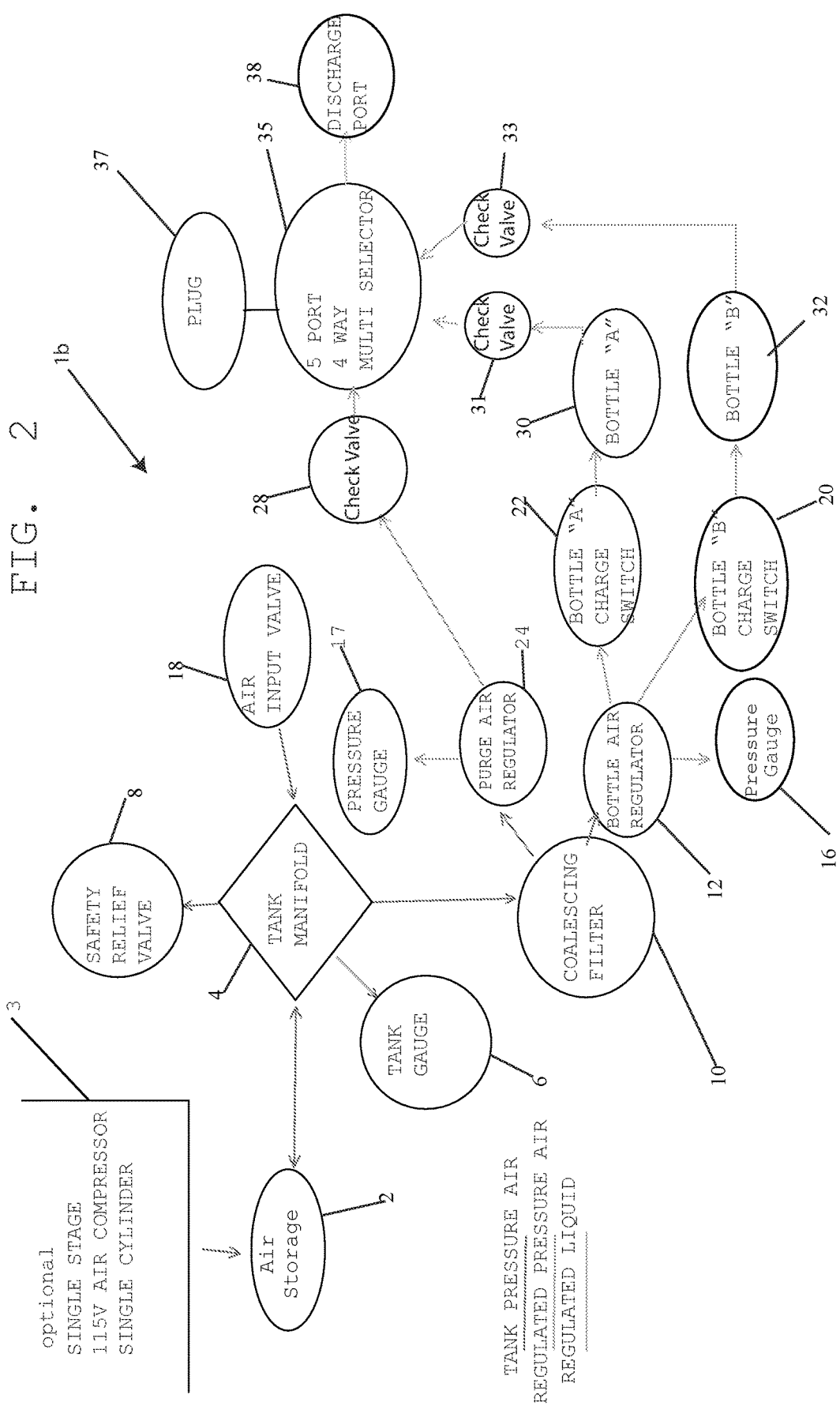
FIG. 2 shows a second block diagram of a second embodiment of the invention.

FIG. 2 is another embodiment of the invention 1b wherein in this view there are similar components to that shown in FIG. 1. All of the components numbered the same are the same components in purpose and function. However, in this view coalescing filter 10 has connected to it both bottle air regulator 12 as well as a purge air regulator 24. This purge air regulator is coupled directly to coalescing filter 10 so that the presences of the five (5) port four (4) way multi selector 35 can take the place of at least the purge air switch 14. The five port 4-way multi selector switch 35 also takes the place of the bottle selection switch 34, as well as the wash, rinse and purge switch 36. In the case of the five (5) port four (4) way multi selector switch 35, a plurality of check valves 28, 31 and 33 are configured to connect this device to the different feeds. These check valves 28, 31 and 33 are configured as one-way check valves which are configured to keep any fluid from flowing into the air lines or to keep any air from flowing back into the fluid lines as well. For example, check valve 28 is positioned between selector 35 and purge air regulator 24. Check valve 31 is positioned between bottle "A" having the cleaning solution and the selector 35. Check valve 33 is positioned between bottle "B" and selector 35. In addition, coupled to selector 35 is a plug 37 which is coupled to at least one output, and a discharge port 38 coupled to another port of the selector 35.

The output of the discharge port can be any one of the cleaning solution from bottle "A" 30 or the rinsing solution from bottle "B" 32, or air from the purge air regulator 24.

Figure 3:
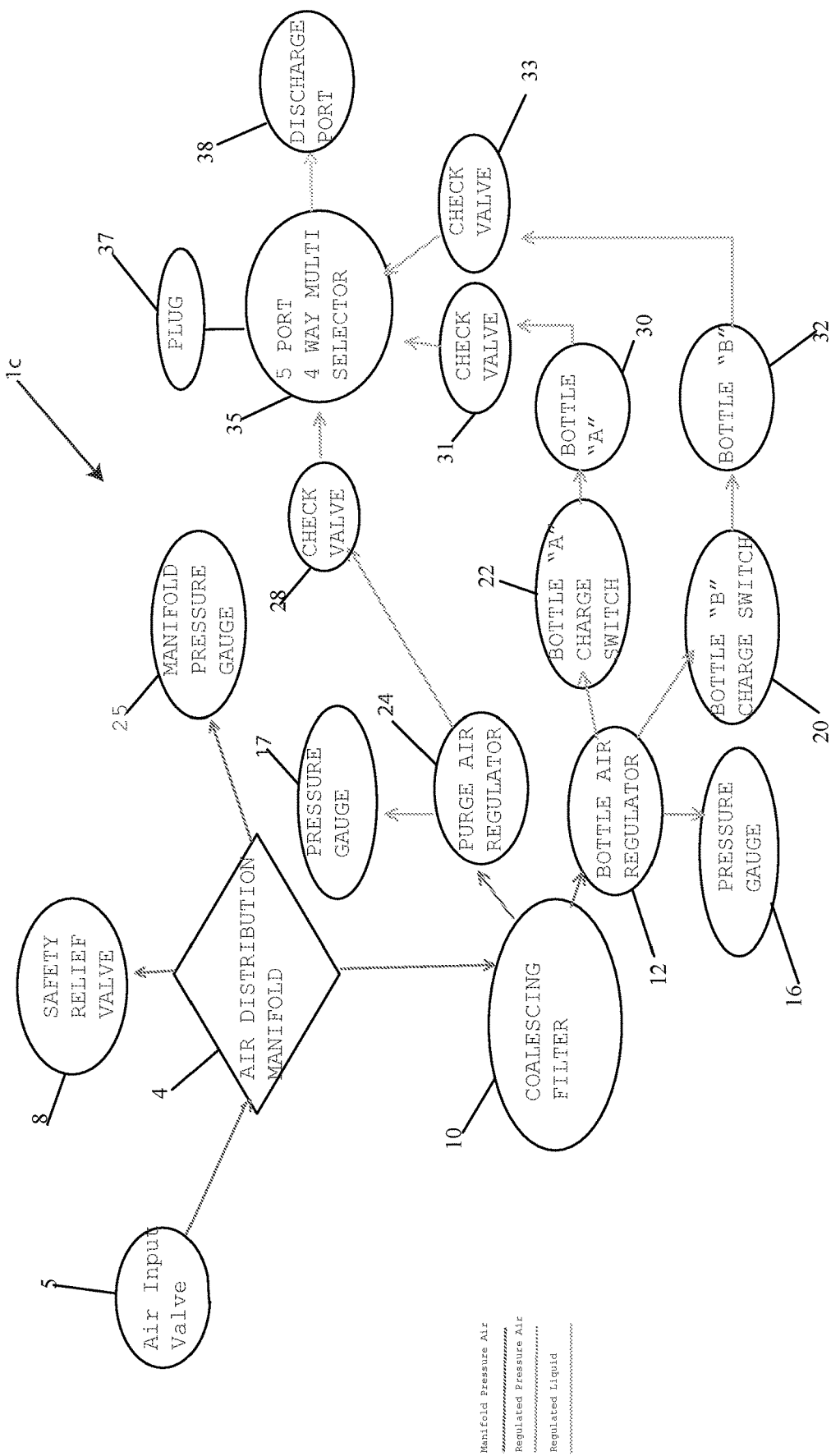
FIG. 3 shows a third block diagram of the third embodiment of the invention.

FIG. 3 is another embodiment of the invention 1c which is configured to not have either an air storage tank 2 or an input from an optional single stage air compressor. Instead all air pressure is fed from a connection by the air input valve 5. Thus, there is no need for the air tank 2 or the additional compressor 3. Thus, this design is a simplified design which makes for a more compact, office staff usable, portable design.

FIG. 4 is a flow chart for the process for cleaning a medical system such as a dental system. The process starts in step S1 wherein a user connects a cleaning system to a medical system. Next, in step S2, the user provides air pressure to the cleaning system by connecting air to the system either by connecting an air storage tank such as air storage tank 2 to a tank manifold such as tank manifold 4. Alternatively, an in-house air pressure system can be connected to the tank manifold 4 via air input valve 18. Next, in step S3, the user can provide a cleaning solution source to the cleaning system. The cleaning solution source can be in the form of a cleaning solution which is stored in a storage unit such as bottle "A" 30 which is coupled to discharge port 38. This cleaning solution is provided under pressure such as under air pressure wherein this air pressure flows through bottle air regulator 12 to provide air pressure to both bottle "A" and to bottle "B" 32. As discussed above a switch 22 is configured to selectively provide air pressure to bottle "A" 30.

Step S4 includes providing a rinsing solution through the rinsing solution source such as bottle "B" 32 to the cleaning system. Thus, a user can selectively activate switch 20 to provide pressure to release the rinsing solution to flow through the cleaning system and into the medical system to rinse the lines of the medical system after the cleaning solution has passed through the lines of the medical system.

In at least one embodiment, in step S5 the cleaning solution can be injected into the medical system wherein the cleaning solution can then sit inside the lines of the medical system and treat the biological residue inside of the lines. In at least one embodiment the cleaning solution is made from a bleach or chlorine-based solution. In another embodiment the cleaning solution can be made from a bleach and another activating agent. While bleach can be used other components for cleaning can also be used for the cleaning solution.

Once the cleaning solution has settled inside of the lines of the medical system for a predetermined period of time, a user can then shut off the provision of the cleaning solution in step S6. Next, in step S7 these lines can be rinsed. Thus, a user can then selectively switch on the provision of the rinsing solution to the medical system to rinse the set of lines inside of the medical system.

Next, in step S8 the user can switch off the provision of the rinsing solution. Next, in step S9, the user can then switch on the provision of the air to completely flush out and dry the inside of the lines and leave the system clean, dry and ready to use.

Thus, there is provided both a system and process to clean a medical system such as a dental cleaning system which has water-based lines which may have become compromised with biological material through inaction. This system can then thoroughly clean these lines in an economical manner.

Accordingly, while several embodiments of the present invention have been shown and described, it is obvious that many changes and modifications may be made thereunto without departing from the spirit and scope of the invention.

What is claimed is:

1. A process for cleaning at least one pathway of a dental system comprising the following steps:
   providing a portable cleaning system having a five port four way switch;
   connecting said portable cleaning system to the dental system;
   providing air pressure to the cleaning system from a source of pressurized air, wherein the source of pressurized air is configured to provide pressurized air to a first port of the switch;
   pressurizing cleaning solution in a cleaning solution container with air from the source of pressurized air, wherein the cleaning solution container is part of the cleaning system, and wherein the cleaning solution container is configured to provide the pressurized cleaning solution to a second port of the switch;
   pressurizing rinsing solution in a rinsing solution container with air from the source of pressurized air, wherein the rinsing solution container is part of the cleaning system, wherein the rinsing solution container is configured to provide the pressurized rinsing solution to a third port of the switch, and wherein a fourth port of the switch is plugged with a plug;
   switching said switch to provide at least one of said cleaning solution and said rinsing solution to the at least one pathway of the dental system;
   switching said switch to provide a flow of pressurized air to the at least one pathway of the dental system to clear out liquid from the dental system.

2. The process as in claim 1, comprising the steps of:
   switching off provision of cleaning solution; and switching on a provision of rinsing solution to the dental system to rinse a set of lines in the dental system.

3. The process as in claim 2, comprising the steps of:
switching off the provision of the rinsing solution; and
switching on a provision of air pressure to the dental system to flush a set of lines in the dental system of the rinsing solution.

4. The process as in claim 1, further comprising a step of connecting the cleaning system to an existing air pressure system of a dental office.

5. The process as in claim 1, further comprising a step of providing a coalescing filter which is configured to provide air pressure to at least one of a purge air regulator and a bottle air regulator.

6. The process as in claim 5, further comprising a step of separately adjusting air pressure using said purge air regulator or said bottle air regulator.

7. A process for cleaning at least one pathway of a dental system using a cleaning system comprising a pressurized air source, a cleaning solution source comprising a cleaning solution container, a rinsing solution source comprising a rinsing solution container, and a five port four way switch for switching between the air source, the cleaning solution source, and the rinsing solution source, wherein the cleaning solution container is connected to a first port of the switch such that cleaning solution can be delivered to said first port, wherein the rinsing solution container is connected to a second port of the switch such that rinsing solution can be delivered to said second port, wherein the pressurized air source is connected to a third port of the switch such that pressurized air used to flush and dry the at least one pathway can be delivered to said third port, and wherein a fourth port of the switch is plugged with a plug, the process comprising:
connecting the cleaning system to the dental system;
providing air pressure to the cleaning solution container and the rinsing solution container from the pressurized air source;
switching the switch to provide cleaning solution to the at least one pathway of the dental system; and
switching the switch to provide rinsing solution or air pressure to the at least one pathway of the dental system.

8. The process as in claim 7, further comprising a step of providing a coalescing filter which is configured to provide air pressure to at least one of a purge air regulator and a bottle air regulator.

9. The process as in claim 8, further comprising a step of adjusting air pressure using said purge air regulator or said bottle air regulator.

* * * * *